(12) United States Patent
Aizawa et al.

(10) Patent No.: US 8,969,430 B2
(45) Date of Patent: Mar. 3, 2015

(54) BIOCOMPATIBLE CERAMIC-POLYMER HYBRIDS

(75) Inventors: Mamoru Aizawa, Kawasaki (JP); Masahiro Rikukawa, Yokohama (JP)

(73) Assignee: Showa-Ika Kogyo Co. Ltd., Aichi-ken (JP)

( * ) Notice: Subject to any disclaimer, the term of this patent is extended or adjusted under 35 U.S.C. 154(b) by 140 days.

(21) Appl. No.: 12/621,274

(22) Filed: Nov. 18, 2009

(65) Prior Publication Data
US 2010/0152317 A1     Jun. 17, 2010

Related U.S. Application Data

(60) Provisional application No. 61/138,016, filed on Dec. 16, 2008.

(51) Int. Cl.
| | | |
|---|---|---|
| *A61F 2/00* | (2006.01) | |
| *A61L 27/42* | (2006.01) | |
| *A61L 27/56* | (2006.01) | |

(52) U.S. Cl.
CPC .............. *A61L 27/425* (2013.01); *A61L 27/56* (2013.01)
USPC .......................................... 523/115; 523/113

(58) Field of Classification Search
CPC .............................. A61L 27/425; A61L 27/56
USPC ....................................................... 523/115
See application file for complete search history.

(56) References Cited

U.S. PATENT DOCUMENTS

| | | | | |
|---|---|---|---|---|
| 6,302,913 B1 * | 10/2001 | Ripamonti et al. | ........ | 623/16.11 |
| 6,340,648 B1 * | 1/2002 | Imura et al. | ..................... | 501/80 |
| 2003/0065400 A1 * | 4/2003 | Beam et al. | ................ | 623/23.51 |
| 2007/0207185 A1 * | 9/2007 | Hart et al. | ...................... | 424/423 |
| 2007/0224245 A1 * | 9/2007 | Ameer et al. | ................. | 424/426 |

FOREIGN PATENT DOCUMENTS

| | | | | |
|---|---|---|---|---|
| JP | 2004284933 A | * | 10/2004 | ............. C01B 25/32 |
| JP | 2008-156213 A | | 7/2008 | |

OTHER PUBLICATIONS

Komlev et al, 2002, "Porous hydroxyapatite ceramics of bi-modal pore size distribution", Journal of Materials Science: Materials in Medicine, vol. 13, p. 295-299.*

(Continued)

*Primary Examiner* — Peter F Godenschwager
*Assistant Examiner* — David Karst
(74) *Attorney, Agent, or Firm* — Osha Liang LLP

(57) ABSTRACT

A hydroxyapatite ceramic hybrid material includes a hydroxyapatite ceramic structure having pores therein and a biodegradable polymer included in the pores in the hydroxyapatite ceramic structure. The biodegradable polymer can be a poly L-lactic acid polymer. A method for preparing a hydroxyapatite ceramic-biodegradable polymer hybrid material includes preparing a porous hydroxyapatite ceramic containing pores having an average pore diameter of 10 μm or larger; and forming a biodegradable polymer in the pores of the porous hydroxyapatite ceramic. The porous hydroxyapatite ceramic may be prepared by: preparing a slurry comprising hydroxyapatite fibers and heat-degradable particles in a selected solvent; filtering the slurry to obtain a paste; preparing a molded body using the paste; compacting the molded body to produce a green compact; and firing the green compact at a temperature at least 1000° C. to produce a porous hydroxyapatite ceramic structure.

18 Claims, 7 Drawing Sheets

(56) References Cited

OTHER PUBLICATIONS

Aizawa, Mamoru, Machine-generated English translation of JP 2004-284933 A, Oct. 14, 2004.*

Zeng, Haitong, et al., "Analysis of bovine serum albumin adsorption on calcium phosphate and titanium surfaces"; Elsevier Science Ltd., Biomaterials vol. 20 (1999); pp. 377-384.

Uyama, Hiroshi, et al., "Enzymatic Ring-Opening Polymerization of Lactones to Polyesters by Lipase Catalyst: Unusually High Reactivity of Macrolides"; Bull. Chem. Soc. Jpn., 68 (1995); pp. 56-61.

Habelitz, Stefan, et al., "Nitrogen-containing Apatite"; Elsevier Science Limited, PII: S0955-2219 (99) 00048-5. (10 pages), 1999.

Aizawa, M., et al., "In Vivo and In Vitro Evaluation of the Biocompatibility of the Hydroxyapatite-PMMA Hybrid Materials Having Mechanical Property Similar to That of Cortical Bone"; Key Engineering Materials, vols. 216-220 (2002); (4 pages).

Aizawa, Mamoru, et al., "Fabrication of the Hybrid Materials by the Introduction of Poly (Methylmethacrylate) Into the Porous Hydroxy-Apatite Ceramics"; Bioceramics, vol. 12 (Oct. 1999), World Scientific Publishing Co. Pte. Ltd.; pp. 453-456.

Kawata, M., et al., "Development of porous ceramics with well-controlled porosities and pore sizes from apatite fibers and their evaluations"; 2004 Kluwer Academic Publishers (0957-4530); pp. 817-823.

Notice of Reasons for Rejection (Official Action) mailed Dec. 17, 2013, by the Japan Patent Office in corresponding Japanese Patent Application No. 2009-284999, with English translation (10 pages).

Fall Meeting of the Ceramic Society of Japan, vol. 20th, [2G21], 2007; p. 147 (3 pages).

Preprints for the Society of Polymer Science, Japan, vol. 56, No. 1, (2007), p. 2Pf178 (3 pages).

Preprints for the Society of Polymer Science, Japan, vol. 56, No. 1, (2007), p. 2Pe179 (3 pages.

Preprints for the Society of Polymer Science, Japan, vol. 56, No. 1, (2007), p. 21J14 (4 pages).

Preprints for the Society of Polymer Science, Japan, vol. 56, No. 1, (2007), p. 2U16 (4 pages).

Preprints for the Society of Polymer Science, Japan, vol. 56, No. 1, (2007), p. 3Z05 (4 pages).

Journal of Japanese Society for Biomaterials, vol. 23, No. 5, (2005), pp. 336-342 (9 pages).

* cited by examiner

BIOCOMPATIBLE CERAMIC-POLYMER HYBRIDS

CROSS REFERENCE TO RELATED APPLICATIONS

The present invention claims priority, under 35 U.S.C. §119, of U.S. Provisional Application Ser. No. 61/138,016, filed on Dec. 16, 2008. The content of this provisional application is incorporated by reference in its entirety.

FIELD OF THE INVENTION

The present invention relates to composite materials for bone repair or replacement, more particularly to composite materials comprising hydroxyapatite and a biocompatible polymer.

BACKGROUND OF INVENTION

Many medical conditions, such as bone fracture, involve damages to the hard tissues (e.g., bones). Such conditions need materials that can be used to repair the hard tissue damages. With increasing life expectancy, the need for such materials is expected to increase substantially.

The materials used in such repairs often need to have sufficient mechanical strength to substitute for the functions of the damage hard tissues. These materials may be used temporarily, i.e., until the hard tissue repairs itself, or they may be used as permanent replacements. Various materials used in such hard tissue repairs include ceramic materials.

Currently, there are three types of ceramics that are clinically used for such purposes. Bioactive ceramics are materials that can directly bond with host bone. Examples of such materials include hydroxyapatite ($Ca_{10}(PO_4)_6(OH)_2$; HAp). The second type of bioceramics is biodegradable ceramics. These materials can be gradually resorbed in the body. Such biodegradable materials include, for example, tri-calcium phosphates ($Ca_3(PO_4)_2$; TCP). The third type of bioceramics is bio-inert ceramics. These materials are stable in the living body and have high mechanical strength. Examples of bio-inert ceramic materials include alumina ($\alpha$-$Al_2O_3$) and tetragonal zirconium (t-$ZrO_2$).

Hydroxylapatite is a natural composition found in teeth and bones within the human body. Thus, hydroxyapatite (HAp) has an excellent biocompatibility and, therefore, would be a good candidate material for hard tissue replacements or repairs. Indeed, it is commonly used as a filler to replace damaged bone or as a coating to promote bone ingrowth on prosthetic implants. Some medical implants, e.g. hip replacements or dental implants, are coated with hydroxyapatite, and it has been found that hydroxyapatite may promote osseo-integration of these artificial implants.

Because of these favorable properties of hydroxyapatite, there has been an immense interest in further developing and improving this material for medical use. Various methods have been disclosed for modifying hydroxyapatite and other implant materials to improve their bone adhesion and other properties. For example, it has been shown that coating this material with bone morphogenetic proteins can improve cell adhesion and subsequent tissue attachment. See, Zeng, H., et al., Biomaterials 20 (1999): 377 384. Another commonly used modification is nitridation, which improves the hardness of hydroxyapatite and its chemical inertia to the biological environment. See, Habelitz, S., et al., J. European Ceramic Society 19 (1999): 2685 2694, and Torrisi, L., Metallurgical Science and Technology 17(1) (1999): 27 32.

More recently, U.S. Pat. No. 7,211,271 issued to Risbud et al., combines these two approaches (i.e., nitridation and coating with a bone morphogenetic protein or an analog thereof, or DNA encoding such a protein or analog) to produce hydroxyapatite that facilitates the growth of tissues on such materials.

Although hydroxyapatite and modified hydroxyapatite materials have excellent biocompatibilities and beneficial tissue/bone formation stimulating effects, the mechanical strengths, especially the toughness value and Young's modulus, of hydroxyapatite materials are substantially different from those of living cortical bones. As a result, the use of hydroxyapatite in bone repair or replacement may lead to undesired stress around the junctions of these artificial materials and the natural bones. Such undesired stress will eventually lead to junction failures. Thus, there remains a need for new materials that would have the benefits of hydroxyapatite, but with mechanical properties more similar to those of natural bones.

SUMMARY OF INVENTION

One aspect of the invention relate to hydroxyapatite ceramic hybrid materials. A hydroxyapatite ceramic hybrid material in accordance with one embodiment of the invention includes a hydroxyapatite ceramic structure having pores therein; and a biodegradable polymer included in the pores in the hydroxyapatite ceramic structure. The pores may account for 40-70% volume of the hydroxyapatite ceramic structure. In accordance with one embodiment of the invention, the biodegradable polymer is a ploy L-lactic acid polymer, which is formed by enzymatic polymerization catalyzed by a lipase.

Another aspect of the invention relates to methods for preparing a hydroxyapatite ceramic material. A method in accordance with one embodiment of the invention includes preparing a porous hydroxyapatite ceramic containing pores having an average pore diameter of 10 μm or larger; and forming a biodegradable polymer in the pores of the porous hydroxyapatite ceramic. The porous hydroxyapatite ceramic may be prepared by: preparing a slurry comprising hydroxyapatite fibers and heat-degradable particles in a selected solvent; filtering the slurry to obtain a paste; preparing a molded body using the paste; compacting the molded body to produce a green compact; and firing the green compact at a temperature at least 1000° C. to produce a porous hydroxyapatite ceramic structure.

Other aspects and advantages of the invention will be apparent from the following description and the appended claims.

DETAILED DESCRIPTION

Embodiments of the invention relate to bio-ceramic materials that are based on bioactive HAp. The bioactive hydroxyapatite materials in accordance with embodiments of the invention have some mechanical properties similar to those of bones. Some embodiments of the invention relate to HAp and poly-L-lactic acid (PLLA) hybrid materials. The mechanical strength and Young's modulus of these HAp-PLLA hybrid materials are closer to those of the natural bones than HAp. In addition, PLLA is biodegradable and can be resorbed in the body to make space for new bone growth. Some embodiments of the invention relate to methods for preparing and using these hybrid materials.

As noted above, the mechanical strengths and physical properties of hydroxyapatite (HAp) are very different from those of natural bones. As shown in Table 1 below, hydroxyapatite has a larger Young's modulus, but lower fracture toughness, as compared with a natural bone. Therefore, hydroxyapatite is more susceptible to brittle fractures, as compared with a natural bone.

TABLE 1

|  | Young's Modulus (GPa) | Fracture Toughness (MPa · m$^{1/2}$) | Bending Strength (MPa) |
| --- | --- | --- | --- |
| HAp | 86-120 | 0.7-1.2 | 80-250 |
| Cortical Bone | 7-30 | 2-6 | 50-150 |

Figure 1:
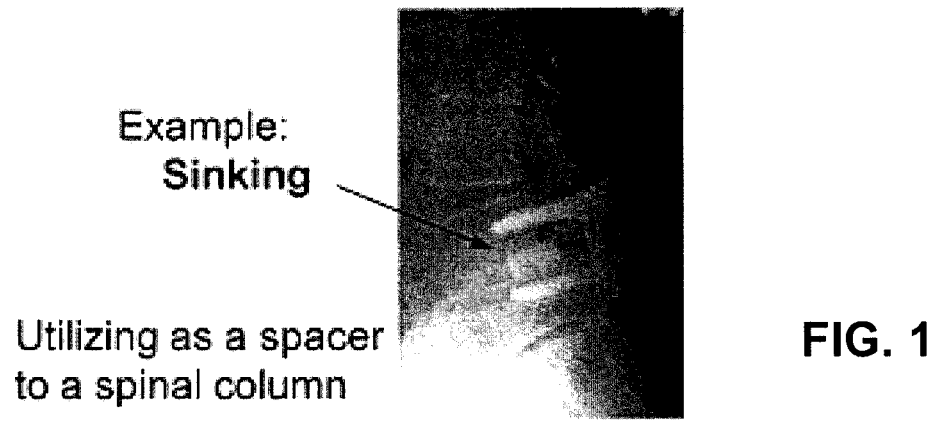
FIG. 1 shows a conventional hydroxyapatite implant in a spine, illustrating the sinking of bone.

Because hydroxyapatite is less flexible and more easily fractured, if HAp is used in bone replacement or repair, unusual stress may develop at the bone-HAp interfaces. Such stress may cause the interfaces to deteriorate overtime, or it may even trigger biological responses (e.g., bone remodeling) that leads to bone loss around the stress interfaces. As a result, the bone replacements may not function properly over time. For example, FIG. 1 shows an example, in which a hydroxyapatite piece is used as a spacer in a spinal column. Over time, the bone and HAp junction deteriorates, resulting in bone sinking.

To overcome the problems described above, it would be desirable to have HAp ceramic materials that have properties similar to those of natural bones. In this regard, inventors of the present invention have previously reported that the properties of porous HAp can be altered by inclusion of other materials in the pores of the HAp structures. For example, when poly(methylmethacrylate) (PMMA) is introduced into porous HAp, it was reported that the hybrid material has a Young's modulus of ~63 GPa, a fracture toughness ($K_{IC}$) of ~2 MPa·m$^{-1}$, and a bending strength of ~65 MPa. See, Aizawa et al., Bioceramics, vol. 12, p. 453 (1999); and Aizawa et al., *Key Engineer. Mater*, vol. 218-220, p. 465-468 (2002). Although PMMA is relatively well tolerated in vivo, PMMA is not biodegradable, and, therefore, the pores in HAp ceramics are permanently blocked.

Some embodiments of the invention relate to porous HAp ceramics that include biodegradable polymers. Such hybrid materials have the desired mechanical properties that are similar to the properties of natural bones. In addition, the biodegradable polymers can be degraded and absorbed to make room for new bone growth.

Figure 2:
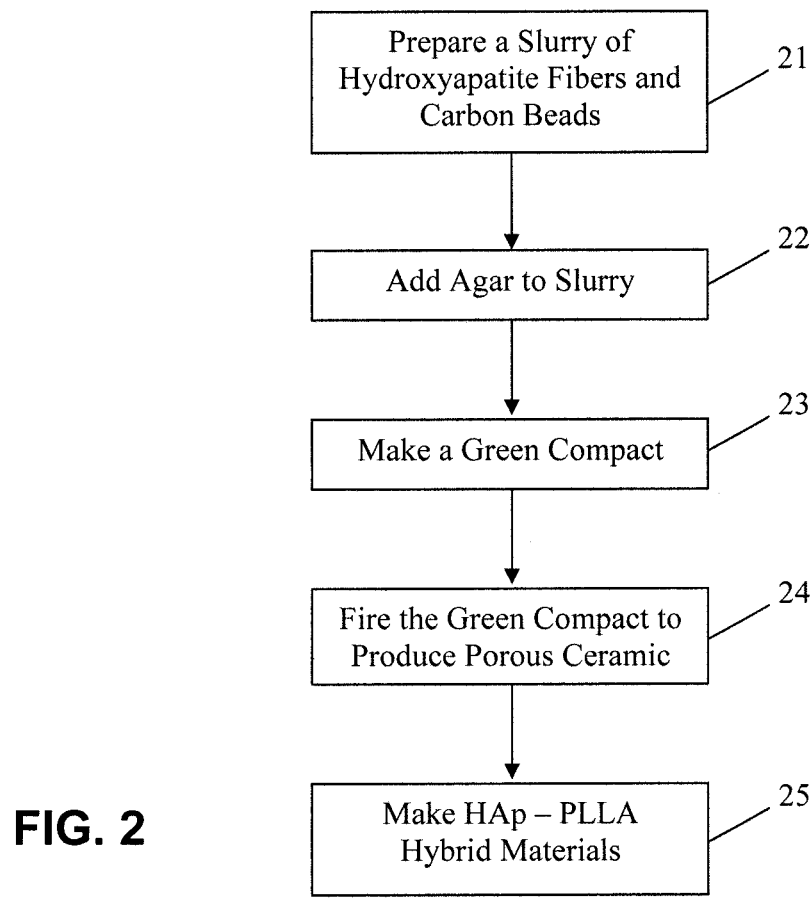
FIG. 2 shows a flow chart illustrating a method for the preparation of porous hydroxyapatite ceramic in accordance with one embodiment of the invention.

FIG. 2 shows a flowchart illustrating a method of the invention for preparing a hybrid of HAp and a biodegradable material. In this example, the biodegradable is poly-L-lactic acid (PLLA). However, one skilled in the art would appreciate that other suitable biodegradable materials may be used instead.

As shown in FIG. 2, a slurry of HAp fibers and carbon beads is prepared (step 21). The HAp fibers may be prepared as disclosed in Kawata et al., "*Development of porous ceramics with well-controlled porosities and pore sizes from apatite fibers and their evaluations*," Journal of Materials Sciences: Materials in medicine, Vol. 15, pp. 817-823 (2004). This paper is referred to as "Kawata publication" in the following description.

For example, HAp fibers may be prepared by precipitation of an aqueous solution containing $Ca(NO_3)_2$ (0.167 mol·dm$^{-3}$), $(NH_4)_2HPO_4$ (0.1 mol·dm$^{-3}$), $(NH_2)_2CO$ (0.5 mol·dm$^{-3}$), and $HNO_3$ (0.1 mol·dm$^{-3}$). This solution contains Ca/P in a ratio of 1.67. This solution is heated at 80° C. for 24 hours and then at 90° C. for 72 hours to produce the apatite fibers having axes about 60-100 μm long. These fibers are collected, for example by filtration. To make a suspension, the apatite fibers are suspended in water at a suitable concentration (e.g., about 1 wt %).

The carbon beads in the slurry may be substituted with any heat-degradable particles. The heat-degradable materials (e.g., carbon beads or plastic beads) will create space between the fibers. After heat treatment, these materials will disappear and leave behind pores within the ceramics. For clarity of description, the following will use carbon beads as examples of the degradable materials. However, one skilled in the art would appreciate that other similar degradable materials (such as plastic beads, etc.) that can leave pores in the ceramics may also be used. Carbon beads are commercially available. For example, Nikabeads® are available from Nippon Carbon Co., Ltd. (Yokohama, Japan) in various diameters (5, 20, or 150 μm).

As shown in the Kawata publication, the sizes of the carbon beads will affect the pore sizes of the final ceramics. For use with embodiments of the invention, carbon beads (or other heat-degradable material beads) of about 10-500 μm in average diameters, preferably about 100-200 μm and most preferably about 150 μm, may be used.

In addition, the amounts of the carbon beads, relative to the amount of the HAp fibers, used will influence the total porosities of the final ceramic. In accordance with embodiments of the invention, a carbon bead to HAp ratio from 1/10 to 50/10 (w/w), preferably from 2/10 to 10/10, more preferably around 5/10, may be used.

Because the carbon beads and the HAp fibers have different densities and tend to separate out in the slurry, it is desirable to add another agent to help disperse these two components (step 22). For example, agar at a suitable concentration (e.g., at 1/10 the amount of the apatite fibers) may be used. With the aid of agar, the fibers and carbon beads can be better dispersed, leading to homogeneous (random) distribution of the pores in the final 3-dimensional ceramic structures. In the absence of agar (or similar suspension aid), the fibers have a tendency to aggregate into a sheet like (2D) structure. The slurry containing agar may be warmed up to a slightly higher temperature (e.g., using a water bath) to help dissolve the agar. One skilled in the art would know how to optimize the amount of agar and what temperature to use without undue experimentation. In addition, materials other than agar may also be used as long as the materials can help with homogeneous dispersion of the HAp fibers and the carbon beads and can be decomposed at high temperature.

To the above slurry (either the apatite slurry or apatite-agar slurry), a co-solvent (such as an alcohol, e.g., ethanol) may be optionally added to change the surface tension of the water solution and to help disperse the particles. The amount of the co-solvent used would depend on the desired effects. For example, when ethanol is used, it may be used at about 10-50% (v/v), preferably about 30% v/v, relative to the total volume (water and ethanol combined volume).

The slurry is used to make green compacts that can be calcined (heated at high temperatures) to make the desired ceramics. For example, the above slurry may be poured into a mold having the desired shape to make a pre-compact. The mold may have a porous or solvent permeable bottom, for example, such that the solvents (e.g., water and ethanol) may be removed, by suction filtration if necessary. In addition to the above described, as noted above, the mixed slurry comprising of HAp fibers and carbon beads can be made more homogeneous by adding a desired amount of agar to the slurry. Agar in the slurry helps to create a homogeneous (random) distribution of pores in the 3D ceramic structure.

The pre-compact body is allowed to dry. Then, it may be further compacted by applying a selected pressure, for example about 10-50 MPa, preferably about 20-40 MPa, more preferably about 30 MPa, to produce a green compact (step 23). The compaction affects the pore sizes in the final ceramics and may also affect the mechanical strength of the final ceramic products.

The compacts can then be calcined (e.g., fired at high temperatures) to produce the ceramics (step 24). The calcination (heating) may follow conventional procedures. The heating may be performed at a temperature about 1000-1500° C., preferably about 1200-1300° C. The calcination, for example, may be performed in an electrical furnace. Furthermore, in accordance with embodiments of the invention, the heating may be conducted in an atmosphere of steam in order to prevent the loss of hydroxyl groups from the hydroxyapatite. The time needed for the calcination (heating) would depend on the size of the green compacts, the temperature used, and other factors. Typically, the curing process may take a few hours, for example from 1-10 hours, preferably around 3-5 hours.

The firing (high temperature curing) cures the HAp fibers into ceramics at the same time vaporizes the carbon beads. As a result, the final HAp structures are left with relative large pores (where the carbon beads were), together with small pores that were created by gaps between the fibers (where no carbon beads were incorporated into the green compacts). Thus, these procedures produce HAp structures with bi-modal pore distributions (i.e., with large pores and small pores).

For example, carbon beads having about 150 μm diameters are found to leave pores of about 100 μm or larger in the HAp ceramics. In addition to these pores, the resultant HAp ceramics also contains smaller pores about 1-5 μm diameters that result from the gaps between the HAp fibers that did not include the carbon beads. That is, these porous HAp ceramics actually have pores with two different size distributions: a group of small pores around several micrometers in sizes and another group with pores of more than 100 μm in sizes. This may be referred to as "bimodal" porous HAp ceramics.

Figure 3:
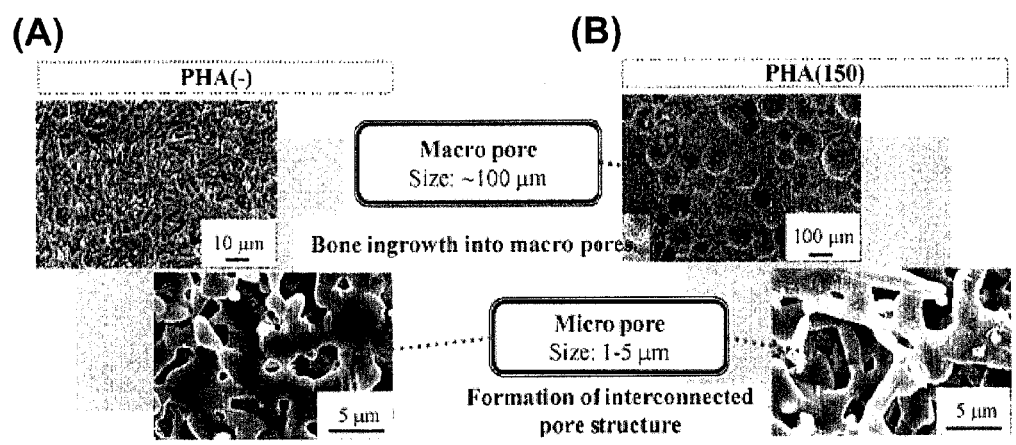
FIG. 3A shows a porous HAp ceramic prepared without inclusion of carbon beads.
FIG. 3B shows porous HAp ceramics prepared with inclusion of carbon beads having diameters of about 150 μm in accordance with one embodiment of the invention.

As shown in FIG. 3 panel (A) on the left, the HAp ceramic was made without added carbon beads. As a result, the pores are small in sizes, in the range of a few μm (e.g., 1-5 μm). In contrast, as shown in FIG. 3 panel (B) on the right, the HAp ceramics prepared with the added carbon beads (150 μm diameters) have larger pores (up to 100 μm or larger), in addition to the small pores (1-5 μm), referred to as macro pores and micro pores, respectively, in FIG. 3.

As noted in the Kawata publication, the total porosities of the ceramic products may be controlled by varying carbon bead sizes and the relative carbon bead/HAp amounts. In addition to the carbon beads sizes and amounts, compaction pressure used in making the green compacts and the firing temperatures used in producing the ceramics will also affect the total porosities of the final products. Among these factors, the carbon-bead diameter has the most influence on the final pore sizes, whereas the compaction pressure and the firing temperatures have less impact on the final porosity of the ceramics.

In accordance with embodiments of the invention, the HAp ceramics may have about 30-80% total porosity, preferably have about 40-70% total porosity. By using carbon beads, these ceramics have large pores that are interconnected. These interconnected pores are desirable for inclusion of the biodegradable polymers and also be new growth of bones when used in vivo.

The percentages of pore volumes will affect the physical strength and mechanical properties of the ceramics. Therefore, if stronger or more rigid ceramics are desired, then smaller amount of carbon beads may be used. On the other hand, if more flexible ceramics or ceramics with large total pore volumes are desired, then larger amounts of carbon beads may be used.

Figure 4:
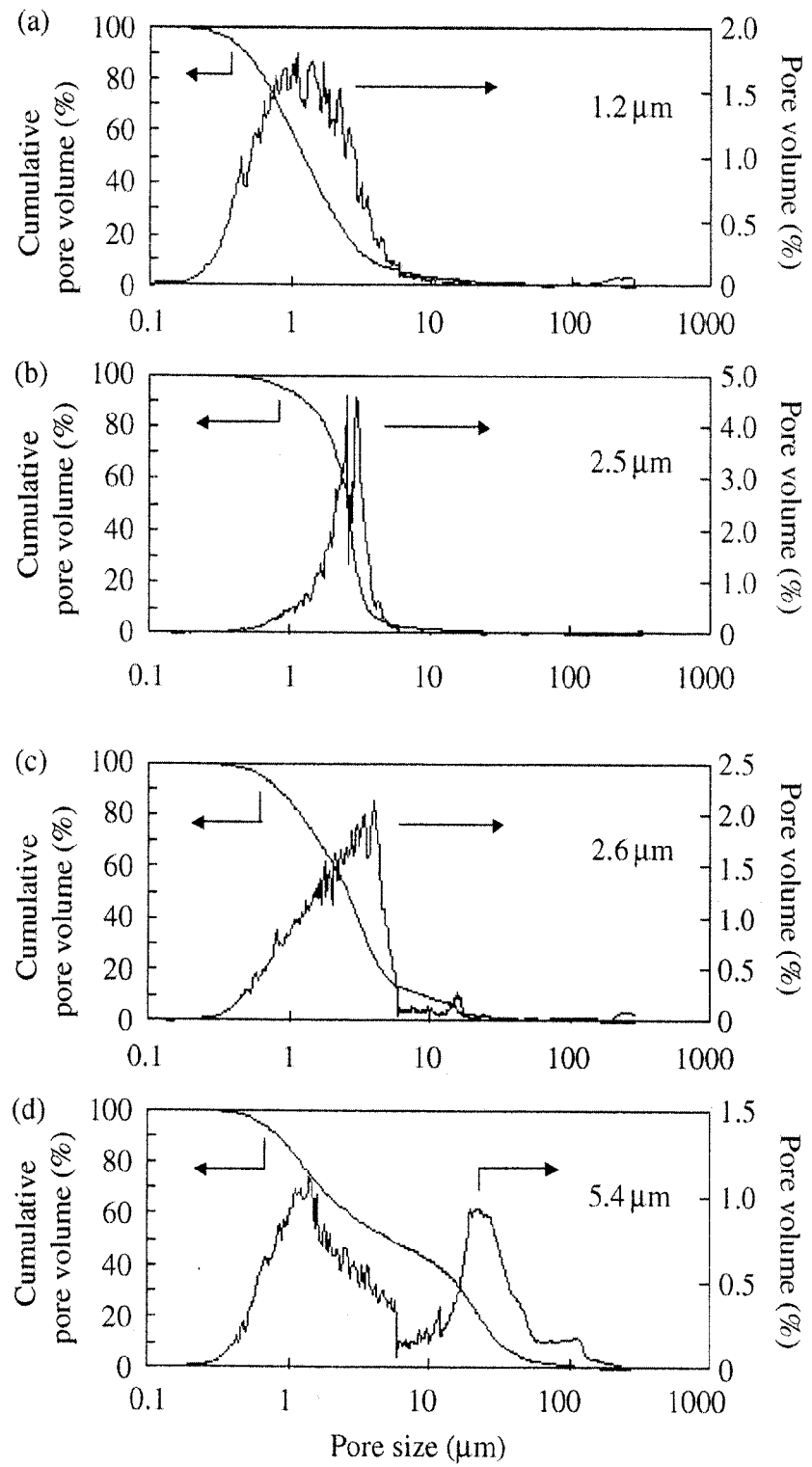
FIGS. 4a-4d show pore-size distributions of HAp ceramics prepared with various carbon beads having different diameters.

FIG. 4 shows pore-size distributions and pore volumes of HAp ceramics prepared with different sizes of carbon beads. As shown in FIG. 4, panel (a), when no carbon beads are included, the resultant ceramics have mostly small pores (those arising from gaps between fibers, the median pore diameter is 1.2 μm). When carbon beads (5 μm) are includes, the resultant ceramics have two populations of pores (Panel b; median pore diameter 2.5 μm). When carbon beads of 20 μm diameters are included, the resultant ceramics have pores shifted to larger pore sizes (Panel c; median pore diameter 2.6 μm). FIG. 4, panel (d) shows the ceramics with carbon beads of 150 μm diameters included have a median pore diameter of 5.4 μm. However, these ceramics have two populations of pore sizes, one of which have pores of less than 10 μm sizes, while the other clearly shows pore diameter distribution between 10 and over 100 μm.

As noted above, the HAp porous ceramics prepared with inclusion of carbon beads (e.g., 150 μm diameters) may have large pores with diameters on the order of ~100 μm (see FIG. 3 and FIG. 4d). The large pore sizes result in many connected channels in the porous HAp ceramics. Such connected channels are desirable because they facilitate the inclusion of biodegradable polymers in such ceramics, according to embodiments of the invention described below. In addition, these connected channels would also facilitate the formation of bone tissues inside the ceramic after such devices are implanted in a patient.

The ceramic product may be further worked on (e.g., cut or polishing) to produce the final desired ceramic products. The further working step may produce a ceramic product in a shape for the intended use.

Referring again to FIG. 2, in accordance with embodiments of the invention, the porous HAp ceramics may be further modified by inclusion of one or more biodegradable materials in the pores (especially, the connected channels formed by these pores) (step 25). Examples of suitable biodegradable materials may include esters, amides or the like. In accordance with embodiments of the invention, the biodegradable materials are preferably esters; more preferably, the biodegradable materials are esters of naturally occurring acids, such as L-lactic acid, glycolic acid, citric acid, etc. The biodegradable polymers may also be prepared from a mixture of these materials, such as a mixed polymer of lactic acid and glycolic acid. In the following description, poly-L-lactic acid esters are used as examples of such biodegradable materials. However, one of ordinary skill in the art would appreciate that embodiments of the invention may use any suitable biodegradable materials known in the art.

In accordance with some embodiments of the invention, poly lactic acid esters may be incorporated into the pores of porous HAp ceramics by enzyme catalyzed reactions to polymerize the lactic acids. Any suitable enzymes may be used for such polymerization, including lipases. Suitable lipases include lipase CA, lipase PS, or any other suitable lipase. Several lipases are commercially available, such as Amano lipase PS from *Burkholderia cepacia* that is available from Sigma-Aldrich (St. Louis, Mo.).

Figure 5:
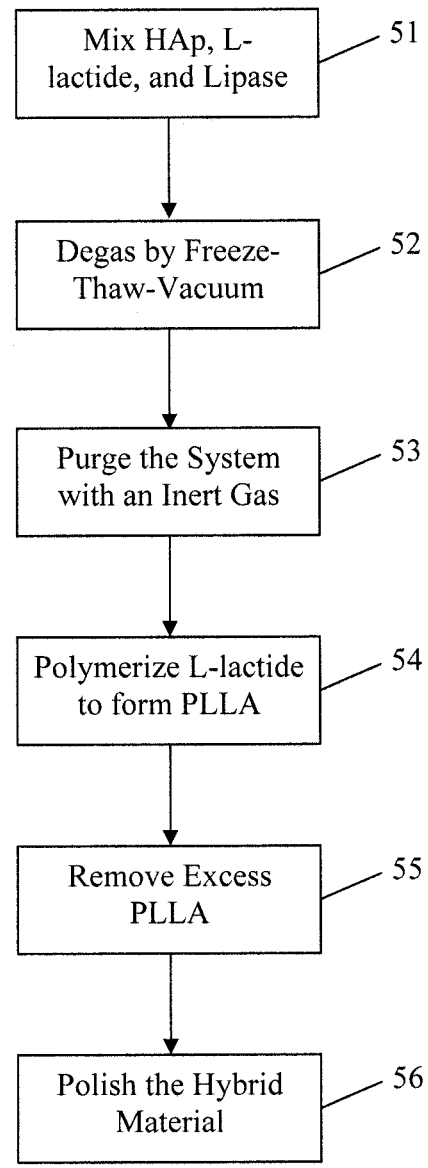
FIG. 5 shows a flow chart illustrating a method for forming a polymer in the pores of a porous HAp ceramic in accordance with one embodiment of the invention.

The polymerization of the lactic acid (or its dimmer, lactide) using an enzyme, such as a lipase (e.g., lipase S), is known in the art. See for example, H. Uyama, K. Takeya, S. Kobayashi, Bull. Chem. Soc. Jpn., 68, 56 (1995). In accordance with embodiments of the invention, PLLA formation can be performed using any suitable protocol and under any suitable conditions. For example, FIG. 5 shows a flow chart illustrating one method for polymerizing lactic acids inside the pores of HAp ceramics in accordance with one embodiment of the invention. As shown in FIG. 5, the HAp, lactic acid (or lactide), and lipase are mixed in a reaction container (step 51).

The substrate and enzyme mixture may be mixed in a solvent (e.g., buffer) that is suitable for the selected lipase. In alternative methods, the substrate (e.g., lactide) solution and the enzyme solution may be separately soaked into the porous HAp ceramics. For example, one may soak the HAp ceramic with the enzyme solution first and allow it to dry (or removing the solution from the pores) after some time for the enzyme to associate with the surface of pores in the ceramic. Then, the resultant ceramic is soaked in a solution containing the substrate (e.g., lactide).

The mixture is degassed by freeze-thaw and vacuuming, which may be repeated 2 or 3 times (step 52). The degassing step is to ensure that the air trapped in the pores within the ceramic is removed and replaced with the reaction solution. The reaction container is then flushed with an inert gas, e.g., nitrogen or argon (step 53). For ease of operation of the freeze-thaw-vacuum cycles, the solution (and the subsequent reaction) may be performed in a reaction vessel having outlets that have valves to facilitate the evacuation of gas and the introduction of the inert gas.

Then, the polymerization is allowed to proceed by keeping the reaction mixture at a proper temperature for a selected duration (step 54), which may depend on the enzyme and reaction conditions used. The commercial suppliers of the lipases often recommend conditions to be used for the reaction. One may follow those recommendations or experiment to improve the efficiency for the particular reaction. Optimization of such reaction is a common practice in the art.

In some experiments, the PLLA polymerization was performed using lactide and lipase at a temperature higher than 100° C. (such as 130° C.) for a selected duration (e.g., 168 h). At this high temperature, the system is under pressure because of the closed reaction container. The high pressure may help force the reaction solution into the pores in the ceramics. Under this condition, the enzyme may not be stable for long. Nevertheless, the inventors found the high temperature conditions to produce good polymerizations. Although the actual mechanisms are not known, it is possible that some or most of the polymerizations may occur without enzyme catalysis under this condition. For example, it is possible that the lipase in the system catalyzes the reaction in the beginning. Once the lactide molecules start to polymerize, each molecule will generate a free hydroxyl group, which can in turn react with another lactide molecule. Thus, the polymerization reaction may proceed in a chain reaction like manner even after the lipase loses activity at high temperature.

After polymerization, the excess PLLA formed is removed (step 55). Then, the HAp-PLLA hybrid may be polished to provide a final product (step 56). Note that the method shown in FIG. 5 is for illustration only. One skilled in the art would appreciate that other variations or modifications of this procedure are possible without departing from the scope of the invention.

Figure 6:
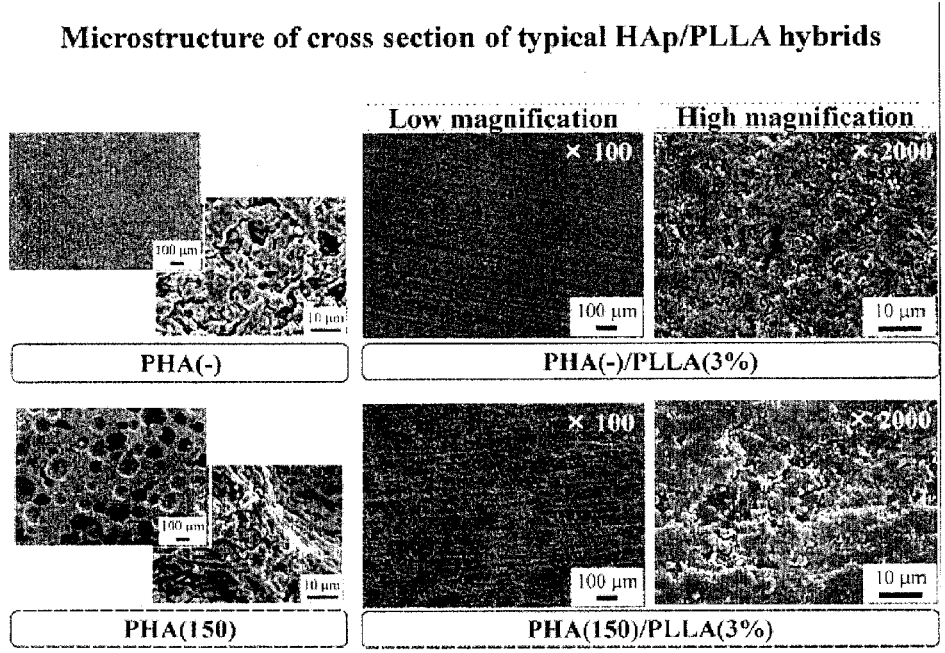
FIG. 6 shows microstructures of HAp and PLLA hybrid materials in accordance with embodiments of the invention.
Figure 7:
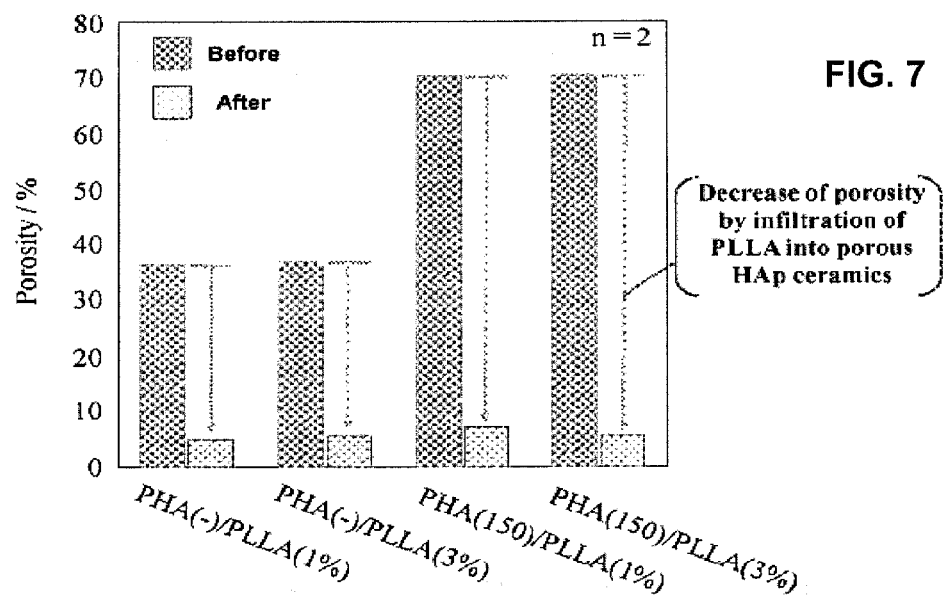
FIG. 7 shows porosity of various HAp-PLLA hybrid materials in accordance with embodiments of the invention.

The porous HAp having biodegradable polymers (e.g., poly-L-lactic (PLLA)) included therein are hybrid materials, which include the HAp ceramic parts and the biodegradable material (e.g., PLLA) parts. Because PLLA fills the pores of the HAp ceramics, the cross section of the resulting hybrids changed from a porous appearance to a dense structure, as shown in FIG. 6 and FIG. 7. In these figures, PHA(−) indicates HAp ceramics without carbon beads added during the preparation, while PHA(150) indicates carbon beads of 150 μm average diameters were added. In addition, PLLA(x %) indicates the x % of lipase (relative to the amount of lactic acid in lactide as 100%) used in the polymerization of PLLA.

FIG. 6 shows scanning electron microscope (scanning EM) images of cross sections of various ceramic (without PLLA) and hybrid (with PLLA) materials. As shown in the left panel in FIG. 6, PHA(−), which is HAp ceramic prepared without carbon beads added therein, includes only small pores (arising from intertwines of Hap fibers) (see also FIG. 3). In contrast, PHA(150), which is prepared with carbon beads (150 μm diameters) added to HAp fibers, has both large (around 100 μm in sizes) and small pores (around a few 1 μm in sizes).

As shown in the right panel in FIG. 6, after formation of biodegradable materials (i.e., PLLA) in the pores using 3% lipase (relative to the amount of lactic acid in lactide), the PHA(−)/PLLA(3%) hybrid shows that most pores are filled with PLLA, as evidenced by smoother cross section surface under the microscope. Similarly, the PHA(150)/PLLA(3%) hybrid no longer has large pores (right panel in FIG. 6), and its cross section is mostly smooth, indicating efficient formation of PLLA in the large pores. In both cases, there are only residual amount of small pores not completely filled in.

FIG. 7 shows a graph illustrating quantitative results of the fillings of PLLA in the ceramic pores. From the chart, it is clear that the HAp ceramics prepared without carbon beads added therein have about 38% total porosities, while those prepared with 150 µm carbon beads have about 70% porosities. After formation of PLLA in the pores, all the hybrid materials have about 5-7% remaining pores. This result suggests that the 5-7% remaining pores are common in all ceramics, regardless of how they were prepared. Furthermore, this result suggest that all large pores in the HPA(150) ceramics are completely filled with PLLA because they also have only 5-7% remaining pores. The results shown in FIG. 7 also suggest that whether the polymerization was carried out with 1% or 3% lipase did not make much difference.

Figure 8:
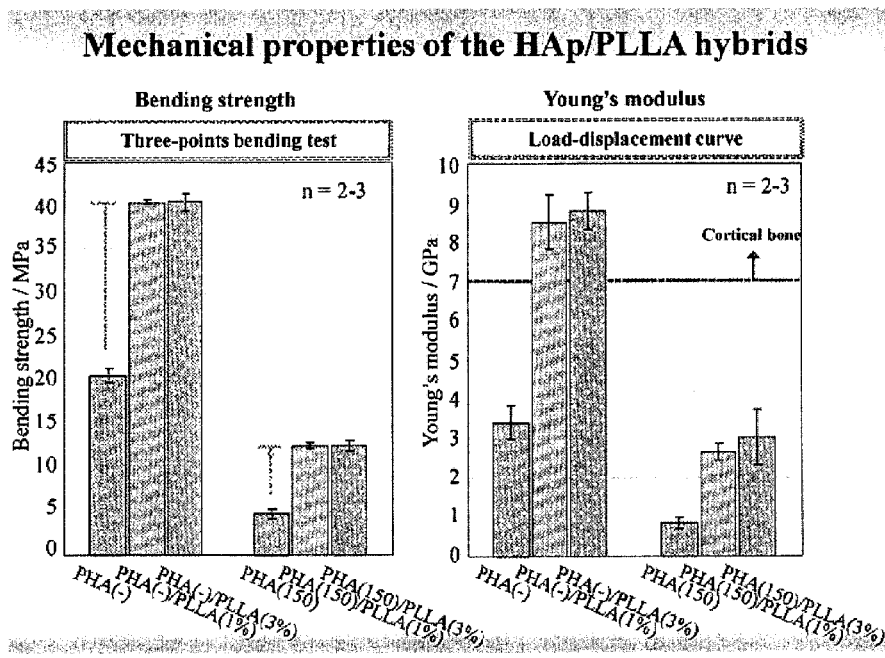
FIG. 8 shows bending strength and Young's modulus of various HAp-PLLA hybrid materials of the invention.

The mechanical or physical properties of HAp ceramics or HAp-PLLA hybrids with large pores are expected to be significantly changed, as compared to small pore HAp ceramics or HAp-PLLA hybrids. As shown in FIG. 8, the bending strengths and Young's modulus of HAp with large pores are much smaller than those without large pores. PLLA formation significantly increases the bending strengths and Young's modulus in both small pore HAp and large pore HAp ceramics. Whether the PLLA polymerization was carried out with 1% or 3% lipase does not seem to make much difference.

The results in FIG. 8 clearly suggest that PLLA formation can be used to improve the bending strengths and Young's modulus of large pore HAp ceramics, making them more closely resemble the physical properties of the natural bone. The inventors have found that large pores in HAp ceramics are important for inducing bone growth in the ceramics (see the discussion below with reference to FIG. 9). However, the presence of large pores in the HAp ceramics significantly lowers the physical strengths of the HAp ceramics, as compared to the HAp ceramic without the large pores. Therefore, PLLA formation provides a viable approach to improve the usefulness of the HAp ceramic materials.

The lower bending strength and Young's modulus of HAp-PLLA hybrids with large pores in accordance with embodiments of the invention render these materials more flexible, as compared to small pore HAp. These large pore HAp-PLLA hybrid materials are intended for applications in which new bone formation is desired. Therefore, the lower physical strengths of these materials will only have temporary impacts. Once new bone growth is achieved, this disparity in physical properties will disappear. Importantly, the hybrids with large pores can facilitate in-growth of bone cells (e.g., osteoblasts) in the interconnected large pores. Therefore, the large pore HAp-PLLA hybrid materials will find applications in situations where new bone formation is desirable.

As shown in FIG. 8, in all cases (HAp ceramics with or without large pores), the inclusion of PLLA increases the mechanical strengths (e.g., bending strength and Young's modulus) of the ceramic materials by a factor of 2 or more. These results validate the concept of using biodegradable materials to alter the mechanical properties of HAp ceramic materials. Furthermore, these results indicate that one can control the pore sizes and/or the degree of biopolymer formation to achieve a desired combination of properties. For example, one may use smaller carbon beads (e.g., 20, 50, or 100 µm diameters) to produce porous ceramics with smaller pores that are still large enough for bone infiltration, while keeping the mechanical properties of the HAp-PLLA hybrid materials closer to those of the natural bone.

The HAp-PLLA hybrid materials incorporate the desired biocompatibility of HAp and the biodegradability of PLLA. These materials when used in vivo are expected to have great biocompatibility and the biodegradable PLLA is expected to give way to incoming bone cells, e.g., osteoblasts. Therefore, these materials are expected to be conducive to new bone tissue formation in the pores of the hybrid materials.

To test the biocompatibility and the utility of HAp-PLLA hybrid materials of the invention, these materials were incubated with MC3T3-E1 cells, which are derived from mouse head bone and have been well characterized as osteoblast-like cells. The incubation was performed in α-MEM culture medium containing 10% fetal calf serum, at 37° C., 5% $CO_2$. Briefly, a piece of the hybrid material (about 15.5 mm diameter, 1-1.5 mm thick) is incubated with $3.0 \times 10^4$ MC3T3-E1 cells and monitored for several days. The materials are removed at different times and assessed with scanning EM to see the growth and attachment of the cells over time.

Figure 9:
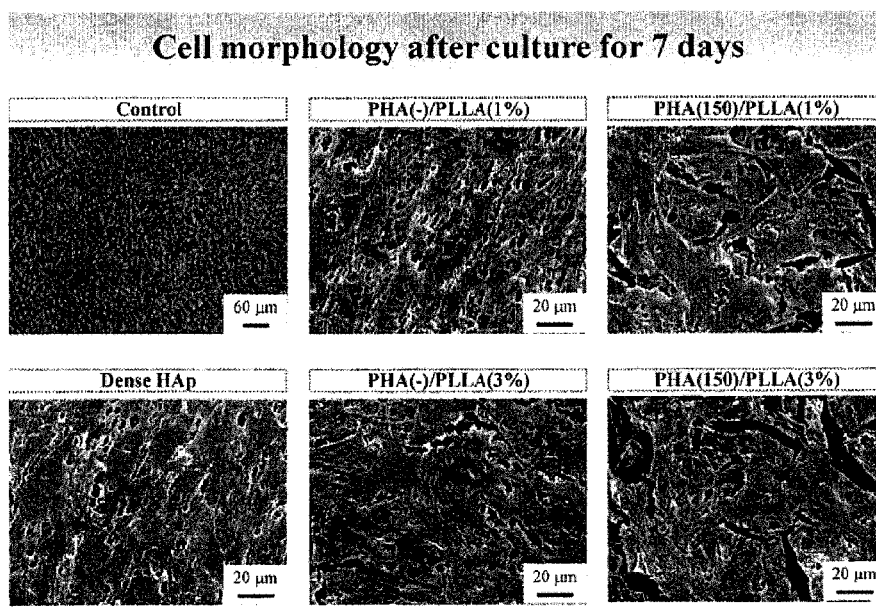
FIG. 9 shows morphology of cells cultured on the HAp-PLLA hybrid materials in accordance with embodiments of the invention for 7 days, together with dense HAp ceramics as a positive control and polystyrene for cell culture plate (Control).

As shown in FIG. 9, the HAp-PLLA hybrid materials in accordance with embodiments of the invention indeed can induce cell growth in the pores that were originally occupied by the biodegradable PLLA. As shown, after 7 days, cells grew in the pores of these materials after resorption of the biodegradable materials. These results indicate that the HAp-PLLA hybrid materials of the invention are non-toxic to the cell and they are conducive to the growth of osteoblast-like cells. Therefore, the HAp-PLLA hybrid materials of the invention would be useful in bone repair and replacement.

The utility of these materials in bone repair and replacement is further tested in vivo by implanting these porous ceramics in rabbit tibia. In these experiments, three rabbits each were used to compare the porous ceramics of this invention with a commercially available ceramic, Apaceram®, (from Pentax Corp. Japan). Apaceram® is a biocompatible hydroxyapatite.

Figure 10:
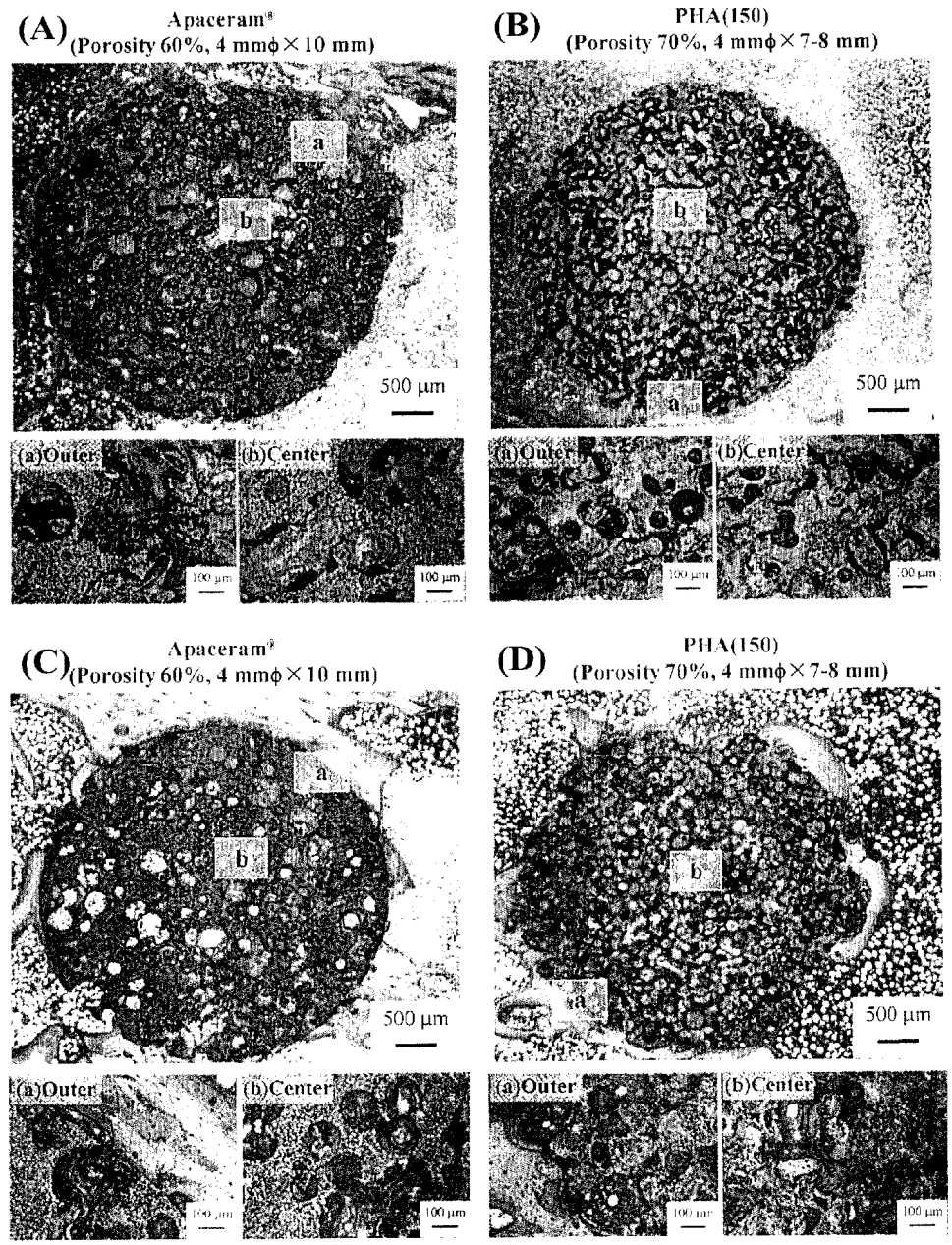
FIGS. 10(A)-10(D) show bone cell growths in the porous ceramics of Apaceram® (FIG. 10(A) and FIG. 10(C)) and bimodal porous HAp ceramics of the invention (FIG. 10(B) and FIG. 10(D)) after being implanted into rabbit tibia for 4 weeks (FIG. 10(A) and FIG. 10(B) and 24 weeks (FIG. 10(B) and FIG. 10(D)).

As shown in FIG. 10(A) (Apaceram®) and FIG. 10(B) (bimodal porous HAp of the invention prepared with 150 µm carbon beads; PHA(150)), 4 weeks after implantation, both ceramics show signs of new bone growth, as evidenced by dark blue stainings with toluidine. FIG. 10(C) (Apaceram®) and FIG. 10(D) (bimodal porous HAp of the invention) are after 24 weeks. These results show that the bimodal porous HAp of the invention is comparable or superior to the currently available biocompatible ceramics (Apaceram®) in terms of osteocunductivity—i.e., conducive to new bone formation in the large pores of the bimodal porous HAp ceramics of the invention.

The superior properties of the bimodal porous HAp of the invention is probably attributable to the fact that the large pores are interconnected, which would be more conducive to bone cell growth inside the ceramic. At the same time, the smaller pores may facilitate the delivery of nutrients to the cells.

Advantages of embodiments of the invention may include one or more of the following. The bimodal pore distribution of the HAp ceramics of the invention includes large pores, which form interconnected channels. These interconnected channels facilitate biopolymer formation therein. More importantly, these interconnected channels are conducive to bone growth inside these ceramic materials. The presence of large pores in the HAp ceramics significantly changes the physical properties of these materials. However, by forming PLLA (or other biodegradable) polymers inside these porous HAp ceramic materials, the physical properties of the porous HAp ceramics are greatly improved, rendering these materials having mechanical properties that are more similar to the natural bones. Thus, when these hybrid materials are used in bone repair or replacement, they will not induce as much stress at the interface. In vivo studies have shown that these HAp-PLLA hybrid materials are non-toxic to the cells and are indeed conducive to the growth of bone cells (e.g., osteoblasts).

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A hydroxyapatite ceramic hybrid material, comprising:
   a hydroxyapatite ceramic structure produced by heating a mixture of fibers and carbon beads, wherein the fibers consist of hydroxyapatite, at a high temperature and having pores therein, the pores comprising bead-shaped pores having an average diameter of greater than 10 μm and a second group of pores having an average diameter of less than 10 μm that are created by gaps between the hydroxyapatite fibers; and
   a biodegradable polymer included in the bead-shaped pores and the second group of pores in the hydroxyapatite ceramic structure such that porosity of the hydroxyapatite ceramic hybrid material is about 5% to 7%.

2. The hydroxyapatite ceramic hybrid material of claim 1, wherein the biodegradable polymer is a poly L-lactic acid polymer.

3. The hydroxyapatite ceramic hybrid material of claim 1, wherein the biodegradable polymer is a poly glycolic acid polymer.

4. The hydroxyapatite ceramic hybrid material of claim 1, wherein the biodegradable polymer is a mixed polymer comprising L-lactic acid and glycolic acid.

5. The hydroxyapatite ceramic hybrid material of claim 1, wherein the bead-shaped pores have an average size greater than 10 μm and less than 150 μm.

6. The hydroxyapatite ceramic hybrid material of claim 1, wherein the bead-shaped pores and the second group of pores are homogeneously distributed in the hydroxyapatite ceramic structure such that the pores account for 40-70% volume of the hydroxyapatite ceramic structure.

7. The hydroxyapatite ceramic hybrid material of claim 6, wherein the bead-shaped pores have an average size greater than 10 μm and less than 150 μm, and the second set of pores have an average size in a range of 1-5 μm and wherein the biodegradable polymer is a poly L-lactic acid polymer.

8. A method for preparing the hydroxyapatite ceramic hybrid material of claim 1, comprising:
   heating a mixture of fibers and carbon beads, wherein the fibers consist of hydroxyapatite, at a high temperature to produce a hydroxyapatite ceramic structure having pores therein, the pores comprising bead-shaped pores having an average diameter of greater than 10 μm and a second group of pores having an average diameter of less than 10 μm that are created by gaps between the hydroxyapatite fibers; and
   forming a biodegradable polymer in the bead-shaped pores and the second group of pores of the hydroxyapatite ceramic structure such that the porosity of the hydroxyapatite ceramic hybrid material is about 5% to 7%.

9. The method of claim 8, wherein the biodegradable polymer is a poly L-lactic acid polymer.

10. The method of claim 8, wherein the biodegradable polymer is a poly glycolic acid polymer.

11. The method of claim 8, wherein the biodegradable polymer is a mixed polymer comprising L-lactic acid and glycolic acid.

12. The method of claim 8, wherein the forming the biodegradable polymer uses a lipase.

13. The method of claim 8, wherein the heating a mixture of fibers and carbon beads at a high temperature comprises preparing a slurry comprising fibers and carbon beads, wherein the fibers consist of hydroxyapatite, in a selected solvent; filtering the slurry to obtain a paste; preparing a molded body using the paste; compacting the molded body to produce a green compact; and firing the green compact at a temperature higher than about 1000° C. for a selected duration.

14. The method of claim 13, wherein the filtering the slurry and the preparing the molded body are performed in a single step by filtering the slurry into a mould having a filter at the bottom thereof.

15. The method of claim 13, wherein the firing is performed at about 1300° C.

16. The method of claim 13, wherein the slurry further comprises agar to help disperse the hydroxyapatite fibers and the carbon beads.

17. The method of claim 13, wherein the firing is performed in the presence of steam.

18. The method of claim 13, wherein the carbon beads have an average diameter of about 150 μm.

* * * * *